(12) United States Patent
Yang

(10) Patent No.: US 7,397,903 B2
(45) Date of Patent: Jul. 8, 2008

(54) COLLIMATOR AND RADIATION IRRADIATOR

(75) Inventor: Zhao Yang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/579,900

(22) PCT Filed: Nov. 20, 2003

(86) PCT No.: PCT/CN03/00985

§ 371 (c)(1),
(2), (4) Date: May 19, 2006

(87) PCT Pub. No.: WO2005/048845

PCT Pub. Date: Jun. 2, 2005

(65) Prior Publication Data

US 2007/0086576 A1    Apr. 19, 2007

(51) Int. Cl.
G21K 1/04 (2006.01)
G21K 1/02 (2006.01)

(52) U.S. Cl. ...................... 378/152; 378/147
(58) Field of Classification Search .......... 378/145–153
See application file for complete search history.

(56) References Cited

U.S. PATENT DOCUMENTS

| | | | |
|---|---|---|---|
| 4,200,803 A | 4/1980 | Becker et al. | |
| 4,277,685 A | 7/1981 | Covic et al. | |
| 4,419,585 A | 12/1983 | Strauss et al. | |
| 5,166,531 A * | 11/1992 | Huntzinger | 250/505.1 |
| 5,436,958 A | 7/1995 | Taylor | |
| 5,438,454 A | 8/1995 | Ludewigt et al. | |
| 5,748,703 A * | 5/1998 | Cosman | 378/152 |
| 6,052,430 A | 4/2000 | Siochi et al. | |
| 6,108,400 A | 8/2000 | Siochi | |
| 6,330,300 B1 | 12/2001 | Siochi | |
| 6,449,340 B1 | 9/2002 | Tybinkowski et al. | |

(Continued)

FOREIGN PATENT DOCUMENTS

JP    2002-355242    12/2002

(Continued)

OTHER PUBLICATIONS

Xiaodong Xu et al.; Patent Application "Collimator, X-Ray Irradiator, And X-Ray Apparatus" filed Nov. 4, 2004; U.S. Appl. No. 10/982,114; 17 pgs.

*Primary Examiner*—Irakli Kiknadze
(74) *Attorney, Agent, or Firm*—Armstrong Teasdale LLP

(57) ABSTRACT

A collimator capable of being reduced in its external size without sacrificing an aperture is to be provided. To this end, the collimator comprises a pair of first plate members which defines a radiation passing aperture by a spacing between respective opposed end faces, a pair of second plate members which respectively overlap the first plate members at least partially so as to block any other radiation than the radiation passing through the aperture, a pair of third plate members which respectively overlap the second plate members at least partially so as to block any other radiation than the radiation passing through the aperture, an adjusting mechanism which adjusts the aperture by moving the pair of first plate members, and a follow-up mechanism which causes the pair of second plate members to move following the pair of first plate members with movement of the first plate members.

10 Claims, 11 Drawing Sheets

U.S. PATENT DOCUMENTS

| | | |
|---|---|---|
| 6,788,764 B2 | 9/2004 | Saladin et al. |
| 7,095,823 B2 * | 8/2006 | Topolnjak et al. ........... 378/152 |
| 7,133,491 B2 * | 11/2006 | Bernardi et al. ............... 378/57 |
| 2002/0057761 A1 | 5/2002 | Danielsson |

FOREIGN PATENT DOCUMENTS

| | | |
|---|---|---|
| WO | WO-01/54137 A1 | 7/2001 |

* cited by examiner (a)

(b)

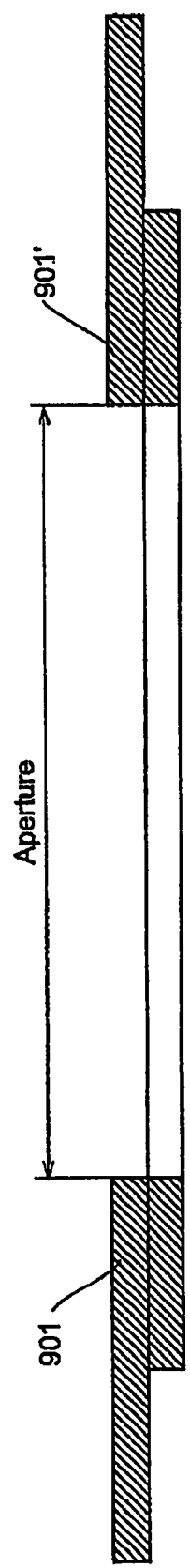

COLLIMATOR AND RADIATION IRRADIATOR

CROSS REFERENCE TO RELATED APPLICATIONS

This application claims benefit of PCT/CN2003/000985 filed Nov. 20, 2003.

BACKGROUND OF THE INVENTION

The present invention relates to a collimator and a radiation irradiator. Particularly, the invention is concerned with a collimator for a radiation, e.g., X-ray, and a radiation irradiator provided with the collimator.

In a radiation irradiator there is used a collimator for controlling the irradiation range of a radiation. The collimator has an aperture which permits a radiation to pass therethrough, and the radiation cannot pass through other than the aperture. Thus, the irradiation range of the radiation is controlled by the aperture. The degree of opening of the aperture can be changed to adjust the irradiation range of the radiation.

As shown in FIG. 10, the aperture-adjustable collimator has a pair of movable plate members having a radiation shielding property, i.e., blades 901 and 901'. The blades 901 and 901' are disposed so that respective end faces are opposed to each other, and are movable in directions opposite to each other in a plane parallel to their surfaces. For widening the aperture, the pair of blades 901 and 901' are moved away from each other, while for narrowing the aperture, the both blades are moved to close to each other. Thus, the aperture becomes maximum when the pair of blades are remotest from each other, and becomes minimum when both blades are closest to each other.

In a collimator having a large aperture adjusting range, there are used blades of a large area. If the blade area is large, an external form of the collimator comes to have a large size corresponding to a maximum moving distance of blade outer edges, as shown in FIG. 11.

In a mammography apparatus which makes fluoroscopy of the breast with X-ray, a collimator assumes a position confronting the face of a subject and so it is preferable that its external form be as small as possible. However, in the case of a mammography apparatus capable of making tomography, an increase in external form of the collimator has heretofore been unavoidable because a large aperture is needed.

SUMMARY OF THE INVENTION

Therefore, it is an object of the present invention to provide a collimator capable of being reduced in its external form without sacrificing an aperture, as well as a radiation irradiator provided with such a collimator.

(1) In one aspect of the present invention for achieving the above-mentioned object there is provided a collimator comprising a pair of first plate members having a shielding property against a radiation and movable in a direction parallel to surfaces thereof, the pair of first plate members defining a radiation passing apertures by a spacing between respective opposed end faces, a pair of second plate members having a shielding property against a radiation and parallel to the pair of first plate members and movable in a direction parallel to surfaces thereof, the pair of second plate members having end faces opposed to each other, the pair of second plate members overlapping the pair of first plate members at least partially so as to block any other radiation than the radiation passing through the aperture, a pair of third plate members having a shielding property against a radiation and parallel to the pair of second plate members, the pair of third plate members having respective end faces opposed to each other with a predetermined spacing, the pair of third plate members overlapping the pair of second plate members at least partially so as to block any other radiation than the radiation passing through the aperture, an adjusting mechanism which adjusts the aperture by moving the pair of first plate members, and a follow-up mechanism which causes the pair of second plate members to move following the pair of first plate members with movement of the first plate members.

(2) In another aspect of the present invention for achieving the above-mentioned object there is provided a radiation irradiator having a radiation source and a collimator for applying a radiation from the radiation source to an object through an aperture, the collimator comprising a pair of first plate members having a shielding property against a radiation and movable in a direction parallel to surfaces thereof, the pair of first plate members defining a radiation passing aperture by a spacing between respective opposed end faces, a pair of second plate members having a shielding property against a radiation and parallel to the pair of first plate members and movable in a direction parallel to surfaces thereof, the pair of second plate members having end faces opposed to each other, the pair of second plate members overlapping the pair of first plate members at least partially so as to block any other radiation than the radiation passing through the aperture, a pair of third plate members having a shielding property against a radiation and parallel to the pair of second plate members, the pair of third plate members having respective end faces opposed to each other with a predetermined spacing, the pair of third plate members overlapping the pair of second plate members at least partially so as to block any other radiation than the radiation passing through the aperture, an adjusting mechanism which adjusts the aperture by moving the pair of first plate members, and a follow-up mechanism which causes the pair of second plate members to move following the pair of first plate members with movement of the first plate members.

In the above aspects of the present invention, since movable blades are constituted by two sets of plate members so that corresponding ones overlap each other, it is possible to reduce the external form of the collimator without sacrificing the aperture.

For changing the aperture symmetrically with respect to the center of the collimator, it is preferable that the adjusting mechanism be able to move the pair of first plate members so as to be closed to and away from each other.

For permitting an appropriate follow-up motion of the pair of second plate members with respect to the pair of first plate members, it is preferable that the follow-up mechanism comprise a rack provided in the first plate member, a gear provided in the second plate member rotatably and engaging with the rack, and a fixed rack provided in the moving direction of the second plate member and engaging with the gear.

For the simplification of construction, it is preferable that the follow-up mechanism comprise an arm member mounted at an intermediate portion thereof to the second plate member and rotatable about the mounting portion in a plane parallel to the plate surface, a groove formed in the first plate member and with which one end of the arm member is engaged, the groove permitting movement of the end of the arm member in a direction perpendicular to the moving direction of the first plate member, and a groove formed in the third plate member and with which an opposite end of the arm member is engaged, the groove permitting movement of the opposite end of the arm member in a direction perpendicular to the moving direction of the second plate member.

For facilitating the adjustment of dose, it is preferable that the radiation be X-ray.

According to the present invention, it is possible to realize a collimator capable of being reduced in its external size without sacrificing the aperture, as well as a radiation irradiator provided with such a collimator.

Further objects and advantages of the present invention will be apparent from the following description of the preferred embodiments of the invention as illustrated in the accompanying drawings.

BRIEF DESCRIPTION OF THE DRAWINGS

FIG. 11 illustrates a fully open condition of an aperture in the conventional collimator.

DETAILED DESCRIPTION OF THE INVENTION

Figure 1:
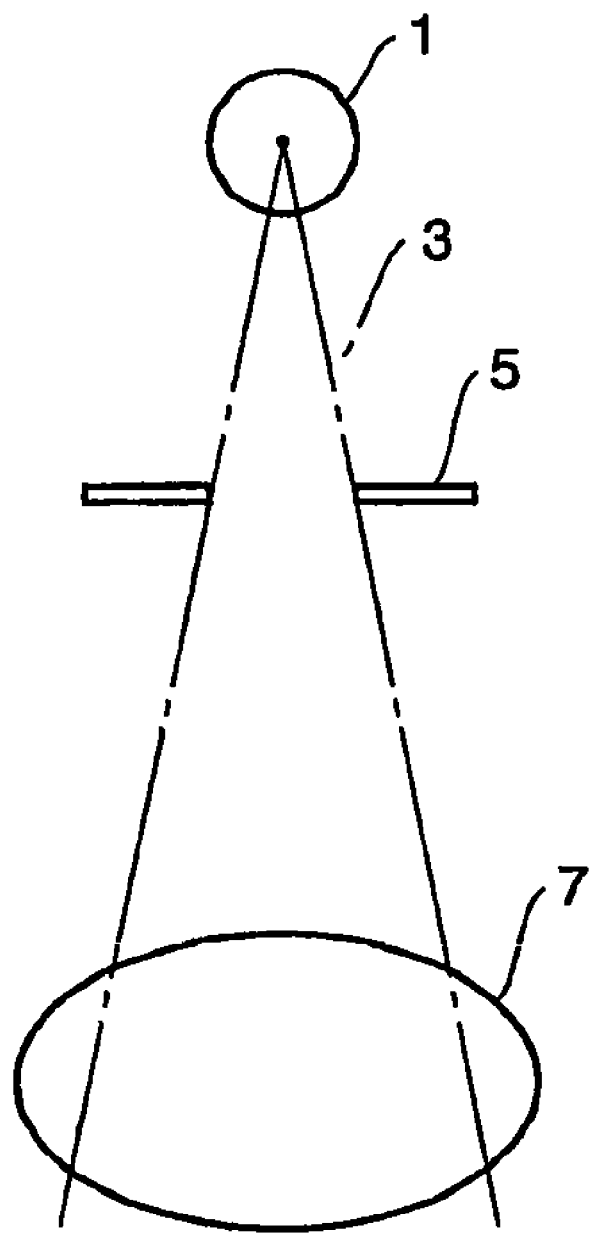
FIG. 1 illustrates a schematic construction of a radiation irradiator.

Embodiments of the present invention will be described in detail hereinunder with reference to the drawings. FIG. 1 illustrates a schematic construction of a radiation irradiator according to an embodiment of the present invention. The construction of this radiation irradiator shows an example of how to carry out the present invention.

As shown in the same figure, the radiation irradiator has a radiation source 1. As the radiation source 1 there is used an X-ray tube for example. The radiation source 1 is not limited to the X-ray tube, but may be any other radiation source capable of emitting a suitable radiation such as β ray or γ ray. The radiation source 1 is an example of the radiation source used in the present invention.

A radiation 3 emitted from the radiation source 1 passes through an aperture of a collimator 5 which embodies the present invention and is applied to an object 7. The object 7 is an object for fluoroscopy using the radiation 3 or an object for therapy using the radiation 3. In fluoroscopy, the radiation which has passed through the object 7 is received by a suitable light receiving means, e.g., a photosensitive plate.

Figure 2:
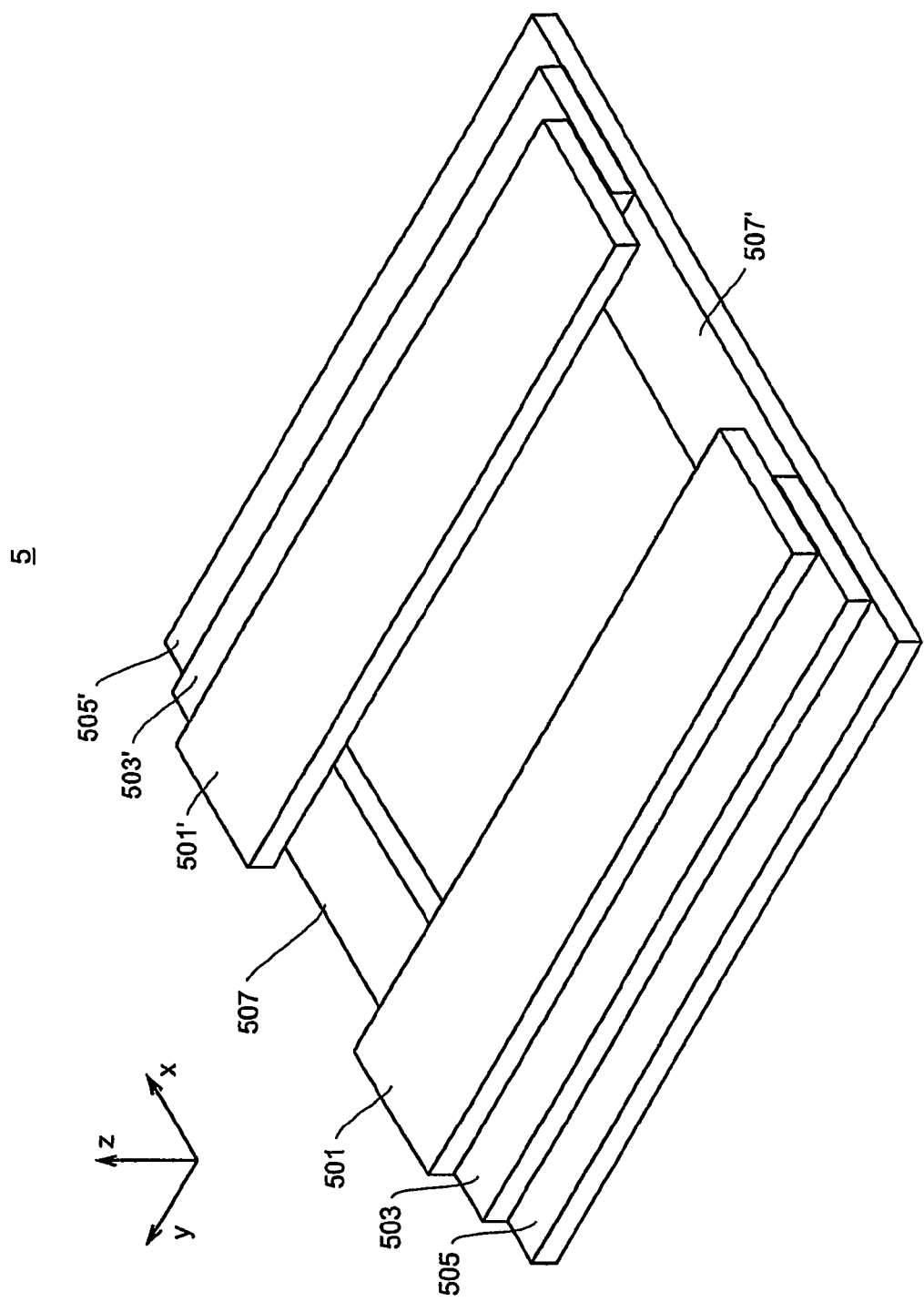
FIG. 2 illustrates the construction of a collimator.

FIG. 2 schematically illustrates the collimator 5, which embodies the present invention. Through the constitution of this, one embodiment of the present invention is described.

As shown in the same figure, the collimator 5 has three pairs of blades 501, 501', 503, 503', and 505, 505'. Each blade is constituted by a quadrangular plate member.

As the material of the plate members there is used a material of a high radiation absorbance such as, for example, lead (Pb) or tungsten (W), whereby each blade comes to have a radiation shielding property.

The blades 501 and 501' are an example of the pair of first plate members in the present invention. The blades 503 and 503' are an example of the pair of second plate members in the present invention. The blades 505 and 505' are an example of the pair of third plate members in the present invention.

In FIG. 2, three directions perpendicular to one another assumed to be x, y, and z. The x direction is a direction of one side of each blade, and the direction will hereinafter be referred to also as the width direction. The y direction is a direction of another side of each blade, and the direction will hereinafter be referred to also as the length direction. The z direction is the thickness direction of each blade. The radiation source 1 lies in the z direction.

The three pairs of blades 501, 501', 503, 503', and 505, 505' overlap one another in the thickness direction. The blades 501 and 501' are upper blades, the blades 503 and 503' are intermediate blades, and the blades 505 and 505' are lower blades.

The lower blades 505 and 505' are supported by a pair of cross beams 507 and 507'. The cross beams 507 and 507' are also constituted by a material of a high radiation absorbance. The cross beams 507 and 507' constitute a picture frame-like frame together with the blades 505 and 505'.

The upper blades 501 and 501' are made movable in the x direction by means of a drive mechanism which will be described later. The blades 501 and 501' are movable so as to be close to and away from each other.

The intermediate blades 503 and 503' are made movable following the upper blades 501 and 501' by means of a follow-up mechanism to be described later. The movement of the blades 503 and 503' is done while maintaining their overlap with the blades 501, 501' and the blades 505, 505' constantly.

The size of the aperture through which the radiation passes is determined in the x direction by the spacing between opposed end faces of the blades 501 and 501' and in the y direction by the spacing between opposed end faces of the cross beams 507 and 507'.

The aperture size in the x direction varies with movement of the blades 501 and 501', while the aperture size in the y direction is fixed. That is, the collimator 5 has an aperture whose size in the x direction can be changed.

Figure 3:
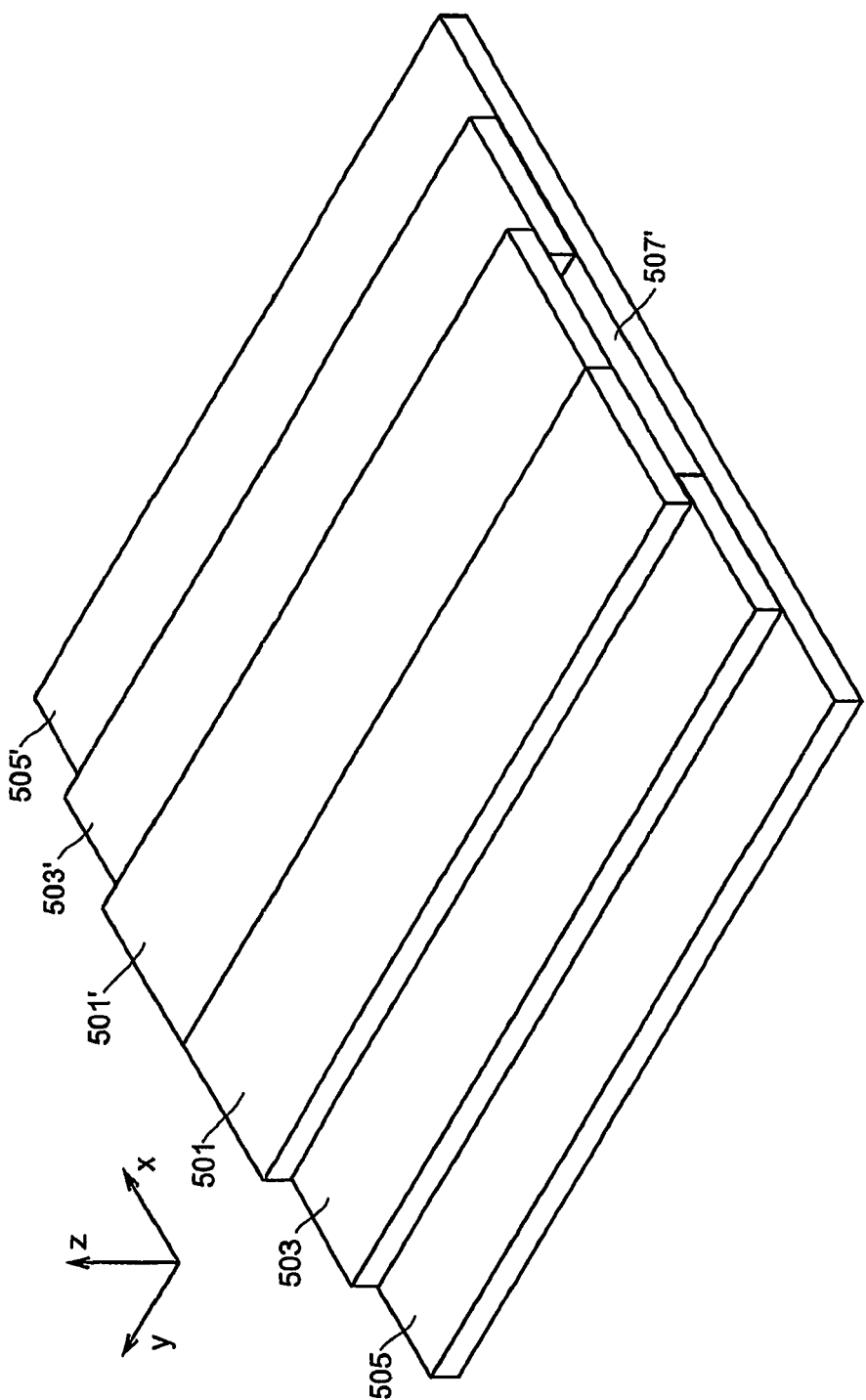
FIG. 3 illustrates the construction of the collimator.
Figure 4:
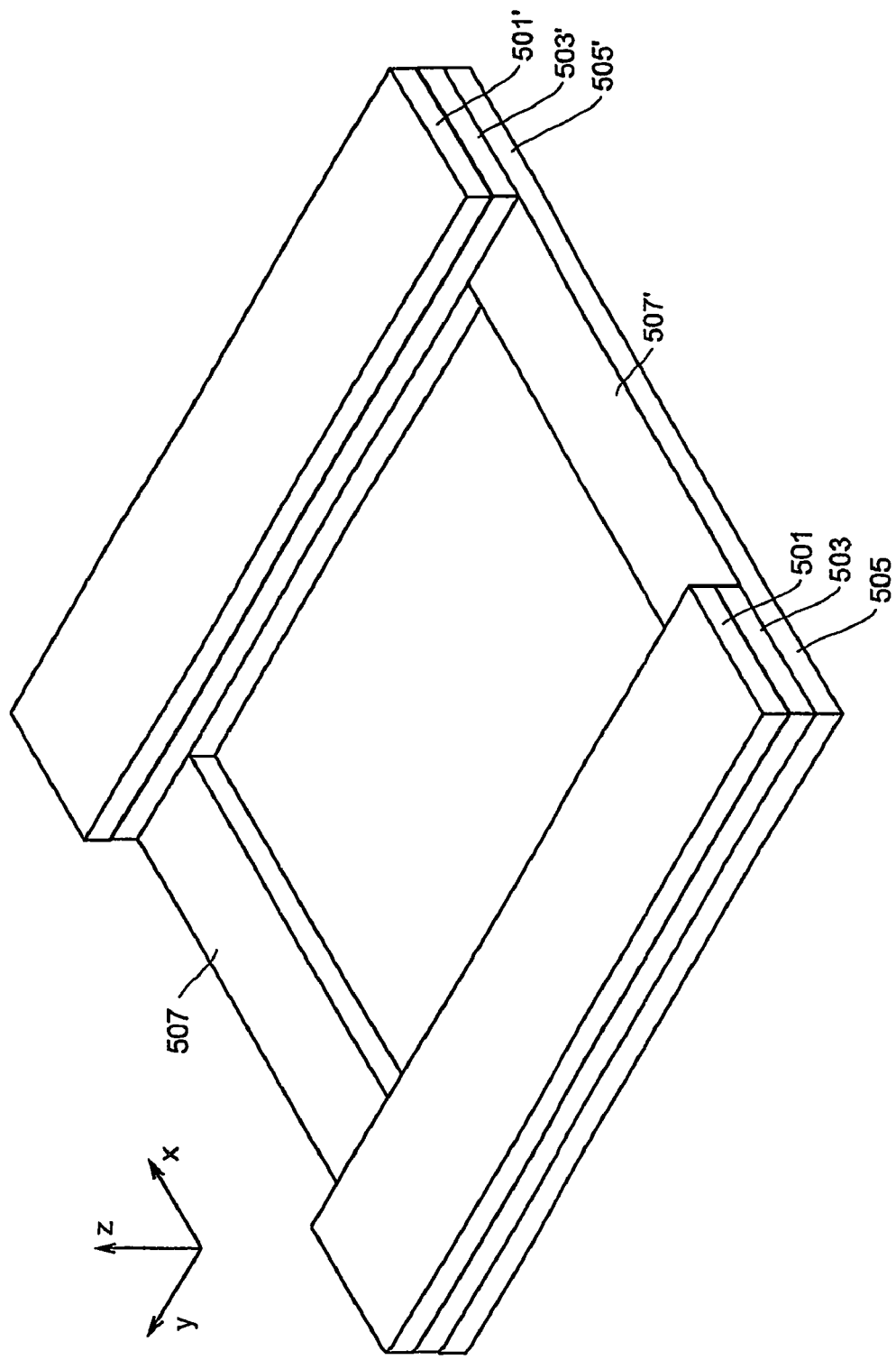
FIG. 4 illustrates the construction of the collimator.

A fully closed state of the aperture is shown in FIG. 3 and a fully open state thereof is shown in FIG. 4. Throughout the whole process of aperture changes, the blades 503 and 503' are kept overlapped with the blades 501, 501' and the blades 505, 505'. Consequently, the passage of any other radiation than the radiation passing through the aperture is blocked.

Figure 5:
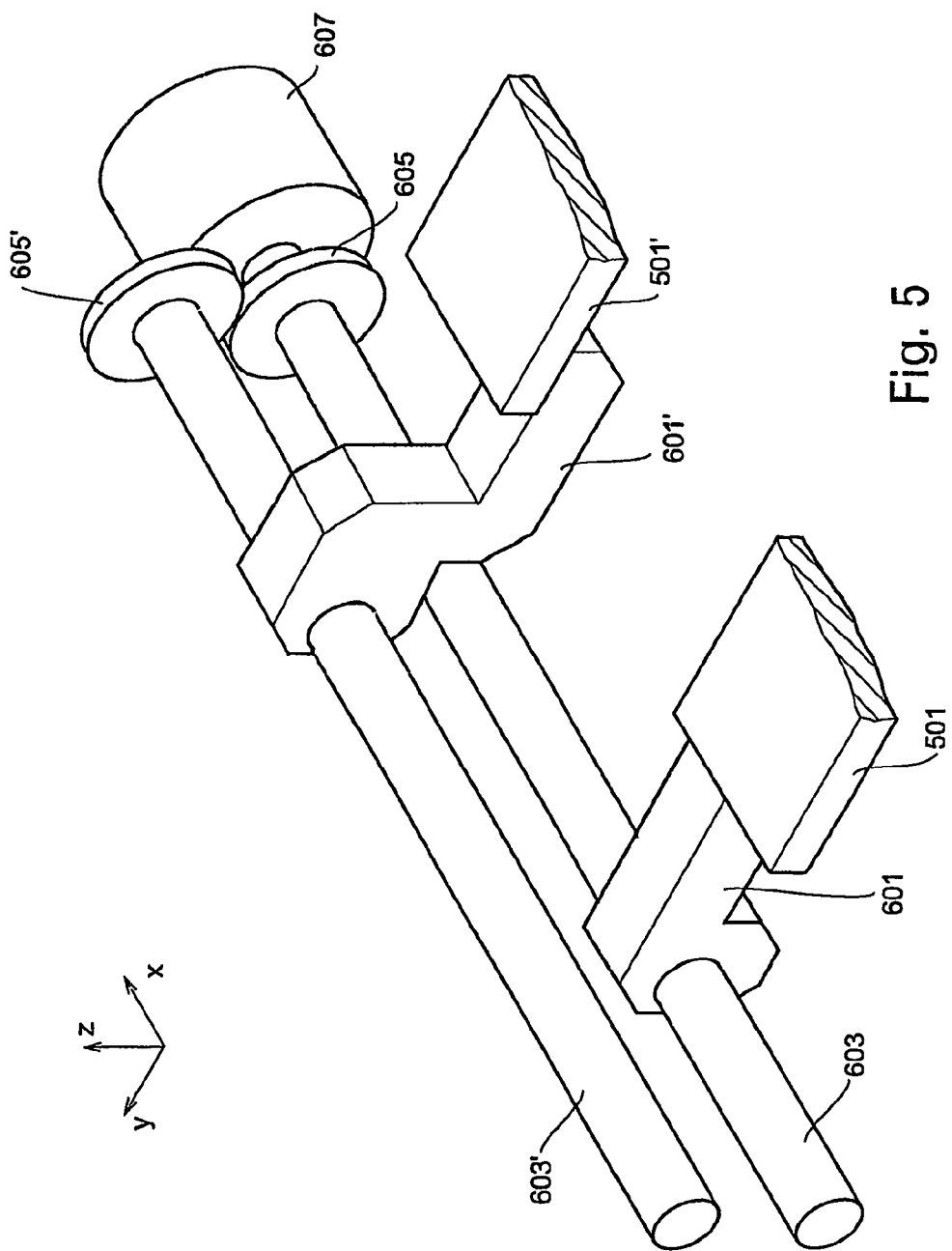
FIG. 5 illustrates a blade drive mechanism.

FIG. 5 schematically illustrates the construction of a drive mechanism for the blades 501 and 501'. This drive mechanism is an example of the adjusting mechanism in the present invention. As shown in the same figure, the blades 501 and 501' have arms 601 and 601', respectively, which extend in the y direction. End portions of the arms 601 and 601' are in engagement with shafts 603 and 603', respectively.

The shafts 603 and 603' are parallel shafts extending in the x direction. Both shafts are spaced a predetermined distance in the z direction. The arm 601' is bent to equalize the height in the z direction of the blade 501' to that of the blade 501.

The shafts 603 and 603' are threaded throughout the overall lengths thereof. The arms 601 and 601' are internally threaded at their portions engaged with the shafts 603 and 603'. Gears 605 and 605' are provided coaxially at one ends of the shafts 603 and 603' respectively. The gears 605 and 605' are in mesh with each other at a gear ratio of 1:1.

The gear 605 is rotated by means of a motor 607. The motor 607, which is a reversible motor, is controlled by a control means (not shown). The control means controls both rotational direction and rotational quantity of the motor 607.

Since the gears 605 and 605' are in mesh with each other, the shafts 603 and 603' rotate in directions opposite to each other. Consequently, the arms 601 and 601' engaged with the shafts 603 and 603' move reverse to each other in the x direction. That is, as the motor 607 rotates in one direction, both arms move to be close to each other, while as the motor 607 rotates in the opposite direction, both arms move away from each other. Their movement quantity is determined by the amount of rotation of the motor 607. By such movements of the arms 601 and 601' there is adjusted the spacing between the blades 501 and 501', i.e., the degree of opening of the aperture. In this way the degree of opening of the aperture can be changed symmetrically with respect to the center of the collimator.

Figure 6:
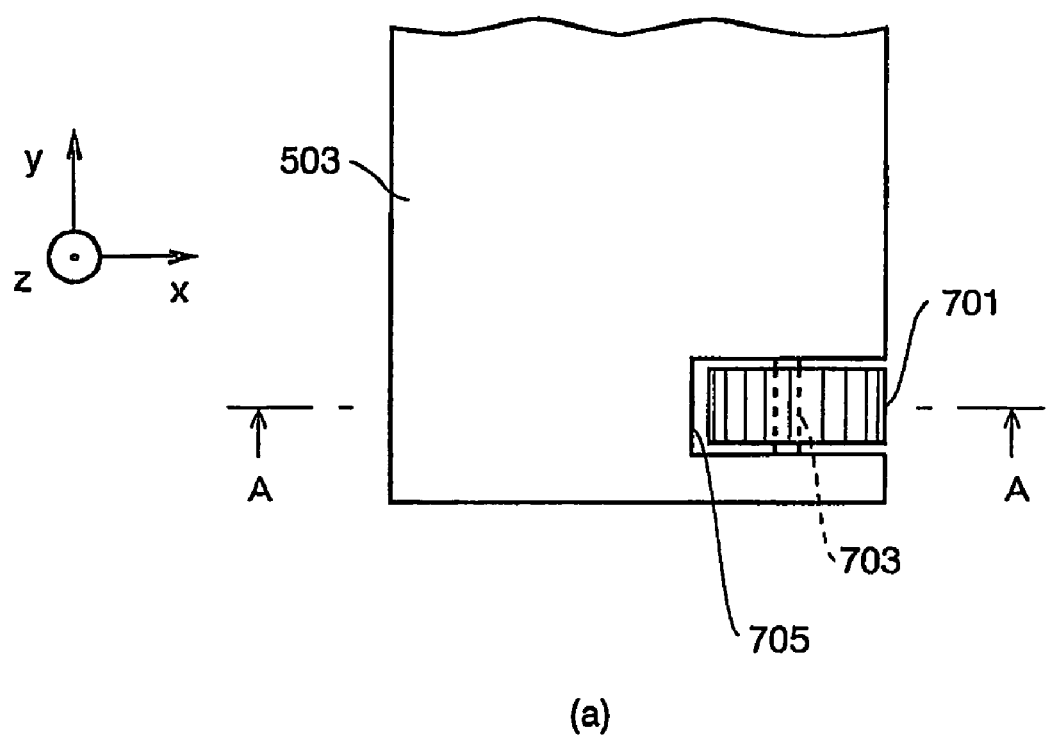
FIG. 6 illustrates a partial construction of a blade.
Figure 6:
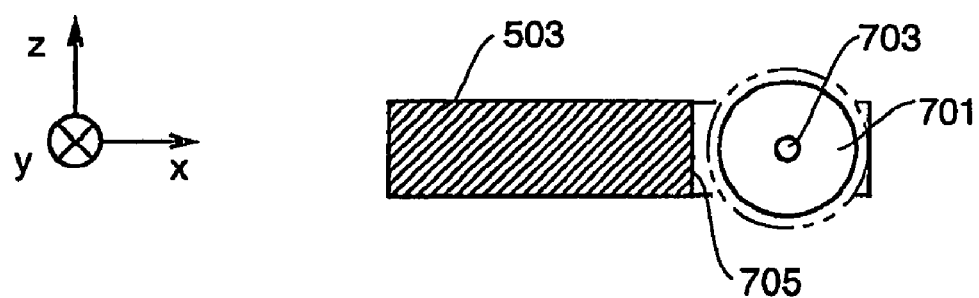

There is provided a follow-up mechanism for allowing the blade 503 and 503' to follow such movements of the blades 501 and 501'. The follow-up mechanism is constituted so as to span the three pairs of blades and the cross beams. As a part of the follow-up mechanism, the blade 503 is constituted as shown in FIG. 6, in which (a) is a plan view and (b) is a sectional view taken on line A-A in (a).

As shown in the same figure, the blade 503 has a gear 701. The gear 701 is mounted rotatably on a shaft 703 which is provided in the blade 503. To be more specific, the shaft 703 is disposed within a cutout portion 705 formed in one end portion in the y direction of the blade 503. The cutout portion 705 is formed in the x direction and the shaft 703 is mounted so as to cross the cutout portion 705 in the y direction. The cutout portion 705 is formed on one side in the x direction of the blade 503. The side where the cutout portion 705 is formed confronts the blade 503' which makes a pair with the blade 503.

The blade 503 has a similar gear also at its opposite end portion in the y direction. That is, the blade 503 has gears at both ends thereof in the y direction. The blade 503' is also of the same construction, provided the blades 503 and 503' are in a relation of specular symmetry.

Figure 7:
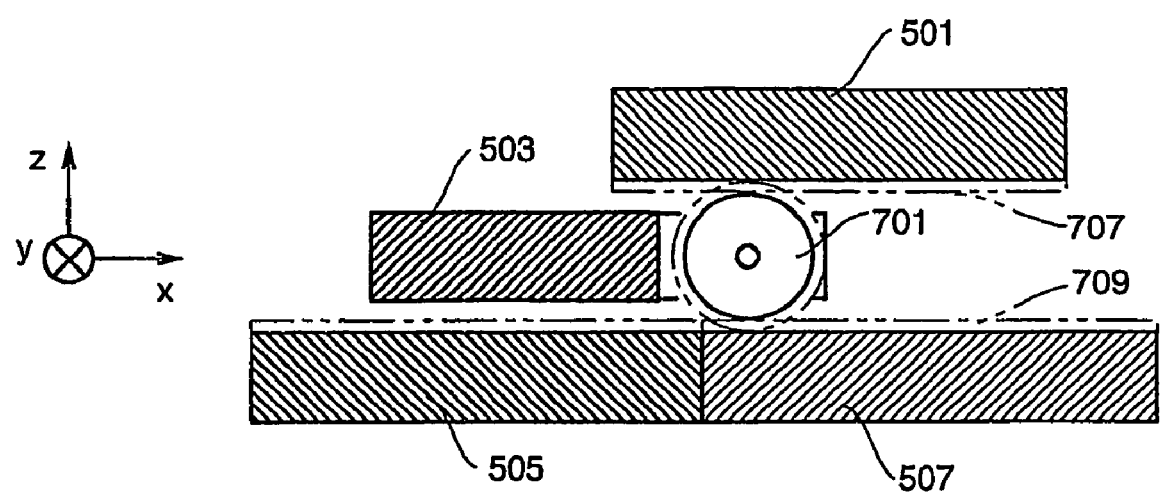
FIG. 7 illustrates the construction of a follow-up mechanism.

FIG. 7 illustrates the construction of the follow-up mechanism schematically. This follow-up mechanism is an example of the follow-up mechanism defined in the present invention. As shown in the same figure, the follow-up mechanism is composed of the gear 701 provided in the blade 503, a rack 707 provided in the blade 501 and meshing with the gear 701, and a rack 709 provided in both blade 505 and cross beam 507 and meshing with the gear 701. The racks 707 and 709 extend in the x direction in parallel with each other.

The gear 701 is an example of the gear defined in the present invention. The rack 707 is an example of the rack defined in the present invention. The rack 709 is an example of the fixed rack defined in the present invention.

As the blade 501 is moved in the x direction, the gear meshing with the rack 707 moves in the same direction while rotating on the rack 709. The blade 503 also moves together with the gear 701. As a result, the blade 503 moves following the blade 501. The distance of the movement of the blade 503 is a half of that of the blade 501.

Such a follow-up mechanism is provided at both end portions of the blades 501, 503, and 505. This is also the case with the mating blades 501', 503', and 505'. With the follow-up mechanism, the follow-up motion of the blades 503 and 503' for the blades 501 and 501' can be done appropriately. Consequently, it becomes possible to make such aperture adjustment as shown in FIGS. 2 to 4.

Figure 8:
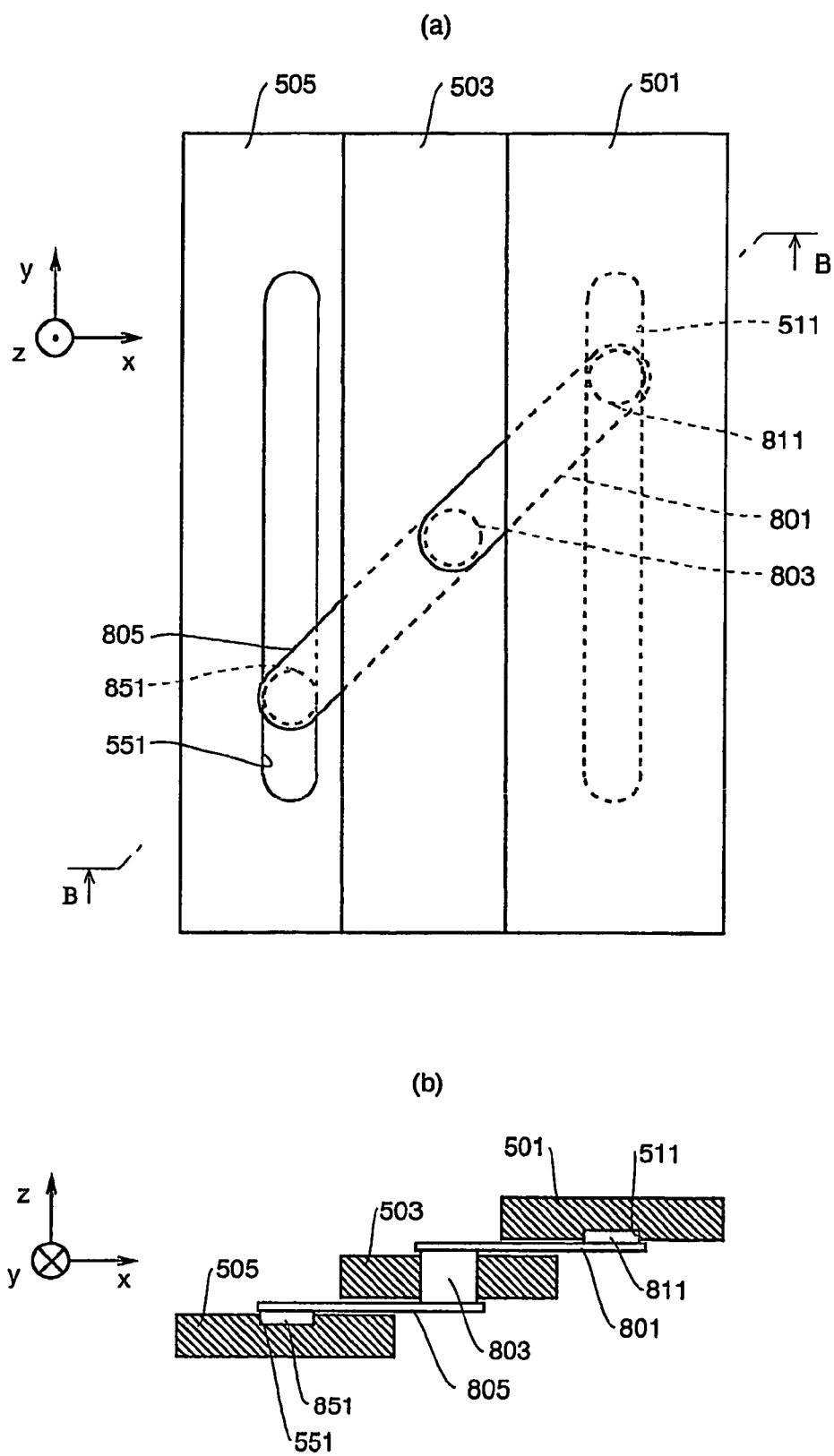
FIG. 8 illustrates the construction of a follow-up mechanism.

FIG. 8 schematically shows another constructional example of a follow-up mechanism. This follow-up mechanism is an example of the follow-up mechanism defined in the present invention. In the same figure, (a) is a plan view and (b) is a sectional view taken on line B-B in (a). As shown in the same figure, the blade 503 is provided with a shaft 803 at its center. The shaft 803 extends through the blade 503 perpendicularly to the plate surface. The shaft 803 is rotatable.

Arms 801 and 805 are fixed respectively to both ends of the shaft 803. The arms 801 and 805 are perpendicular to the shaft 803 and extend in directions opposite to each other. The shaft 803 and the arms 801, 805 form a crank. The extending directions of the arms 801 and 805 in the crank are not coincident with the x direction. The arms 801 and 805 are an example of the arm member defined in the present invention.

The arms 801 and 805 are formed with lugs 811 and 851 at respective free ends. The lugs 811 and 851 extend in the z direction so as to face reverse to each other. The lug 811 is loosely fitted in a groove 511 formed in the blade 501. The groove 511 is positioned on the blade 503 side of the blade 501 and extends in the y direction. The lug 851 is loosely fitted in a groove 551 formed in the blade 505. The groove 551 is positioned on the blade 503 side of the blade 505 and extends in the y direction. The grooves 511 and 551 are an example of the grooves defined in the present invention.

In this construction, when the blade 501 is moved in the x direction, the lugs 811 and 851 move in directions opposite to each other along the grooves 511 and 551, with the result that the crank rotates about the shaft 803.

The position of the blade 505 is fixed, so with the rotation of the crank, the shaft 803 moves in the x direction following the blade 501 and the blade 503 moves in the same direction together with the shaft 803. By setting the lengths of the arms 801 and 805 equal to each other, the distance of the movement of the blade 503 becomes half of that of the blade 501. Thus, this follow-up mechanism becomes simple in construction.

Such a follow-up mechanism is provided also on the side of the mating blades 501', 503', and 505'. As a result, it becomes possible to make such aperture adjustment as shown in FIGS. 2 to 4.

Figure 9:
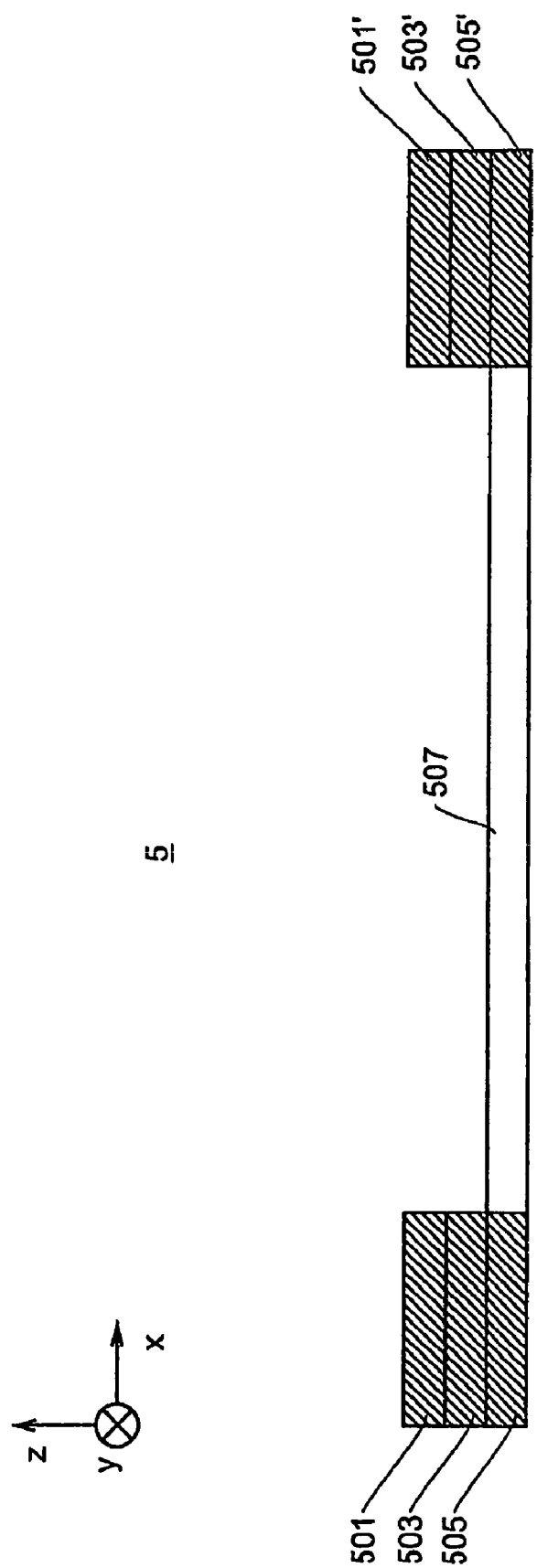
FIG. 9 illustrates a fully open condition of an aperture.
Figure 10:
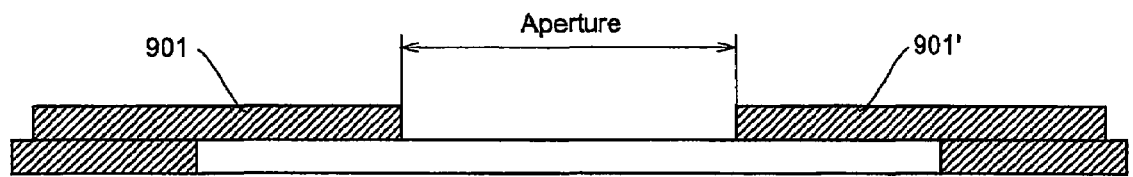
FIG. 10 illustrates a conventional collimator.

In the fully open condition of the aperture shown in FIG. 4, corresponding ones in the three pairs of blades 501, 501', 503, 503', 505, and 505' overlap each other completely. FIG. 9 shows this state in terms of a sectional view. As shown in the same figure, the movable blades 501, 501', 503, and 503' overlap the fixed blades 505 and 505' completely. In this state, outer edges of the movable blades are in alignment with outer edges of the fixed blades, not protruding therefrom. Consequently, an external form of the collimator becomes constant irrespective of the degree of opening of the aperture.

Therefore, if the maximum degree of opening of the aperture is set equal to that in the prior art shown in FIG. 11, it is possible to reduce the external form of the collimator to about three fourths. Alternatively, if the external form of the collimator is made about the same as in the prior art, it is possible to enlarge the maximum value of the aperture to approximately 4/3 time.

Many widely different embodiments of the invention may be configured without departing from the spirit and the scope of the present invention. It should be understood that the present invention is not limited to the specific embodiments described in the specification, except as defined in the appended claims.

The invention claimed is:

1. A collimator comprising:
   a pair of first plate members having a shielding property against a radiation and movable in a direction parallel to surfaces thereof, the pair of first plate members defining a radiation passing aperture by a spacing between respective opposed end faces;
   a pair of second plate members having a shielding property against a radiation and parallel to the pair of first plate members and movable in a direction parallel to surfaces thereof, the pair of second plate members having end faces opposed to each other in the shielding property, the pair of second plate members overlapping the pair of first plate members at least partially so as to block any other radiation than the radiation passing through the aperture;

a pair of third plate members having a shielding property against a radiation and parallel to the pair of second plate members, the pair of third plate members having respective end faces opposed to each other with a predetermined spacing, the pair of third plate members overlapping the pair of second plate members at least partially so as to block any other radiation than the radiation passing through the aperture;

an adjusting mechanism which adjusts the aperture by moving the pair of first plate members; and a follow-up mechanism which causes the pair of second plate members to move following the pair of first plate members with movement of the first plate members.

2. A collimator according to claim 1, wherein the adjusting mechanism is configured to move the pair of first plate members so as to be close to and away from each other.

3. A collimator according to claim 2, wherein the follow-up mechanism comprises:

a rack provided in the first plate member;

a gear provided in the second plate member rotatably and engaging with the rack; and a fixed rack provided in the moving direction of the second plate member and engaging with the gear.

4. A collimator according to claim 1, wherein the follow-up mechanism comprises:

an arm member mounted at an intermediate portion thereof to the second plate member and rotatable about the mounting portion in a plane parallel to the plate surface;

a groove formed in the first plate member and with which one end of the arm member is engaged, the groove permitting movement of the one end of the arm member in a direction perpendicular to the moving direction of the first plate member; and a groove formed in the third plate member and with which an opposite end of the arm member is engaged, the groove permitting movement of the opposite end of the arm member in a direction perpendicular to the moving direction of the second plate member.

5. A collimator according to claim 1, wherein the radiation is X-ray.

6. A radiation irradiator having a radiation source and a collimator for applying a radiation from the radiation source to an object through an aperture, the collimator comprising:

a pair of first plate members having a shielding property against a radiation and movable in a direction parallel to surfaces thereof, the pair of first plate members defining a radiation passing aperture by a spacing between respective opposed end faces;

a pair of second plate members having a shielding property against a radiation, parallel to the pair of first plate members, and movable in a direction parallel to surfaces thereof, the pair of second plate members having end faces opposed to each other, the pair of second plate members overlapping the pair of first plate members at least partially so as to block any other radiation than the radiation passing through the aperture;

a pair of third plate members having a shielding property against a radiation and parallel to the pair of second plate members, the pair of third plate members having respective end faces opposed to each other with a predetermined spacing, the pair of third plate members overlapping the pair of second plate members at least partially so as to block any other radiation than the radiation passing through the aperture;

an adjusting mechanism which adjusts the aperture by moving the pair of first plate members; and a follow-up mechanism which causes the pair of second plate members to move following the pair of first plate members with movement of the first plate members.

7. A radiation irradiator according to claim 6, wherein the adjusting mechanism is configured to move the pair of first plate members so as to be close to and away from each other.

8. A radiation irradiator according to claim 6, wherein the follow-up mechanism comprises:

a rack provided in the first plate member;

a gear provided in the second plate member rotatably and engaging with the rack; and a fixed rack provided in the moving direction of the second plate member and engaging with the gear.

9. A radiation irradiator according to claim 6, wherein the follow-up mechanism comprises:

an arm member mounted at an intermediate portion thereof to the second plate member and rotatable about the mounting portion in a plane parallel to the plate surface;

a groove formed in the first plate member and with which one end of the arm member is engaged, the groove permitting movement of the one end of the arm member in a direction perpendicular to the moving direction of the first plate member; and a groove formed in the third plate member and with which an opposite end of the arm member is engaged, the groove permitting movement of the opposite end of the arm member in a direction perpendicular to the moving direction of the second plate member.

10. A radiation irradiator according to claim 6, wherein the radiation is X-ray.

* * * * *